(12) United States Patent
Kawagishi et al.

(10) Patent No.: US 11,238,588 B2
(45) Date of Patent: Feb. 1, 2022

(54) MEDICAL DIAGNOSIS SUPPORT APPARATUS, INFORMATION PROCESSING METHOD, MEDICAL DIAGNOSIS SUPPORT SYSTEM, AND PROGRAM

(71) Applicant: CANON KABUSHIKI KAISHA, Tokyo (JP)

(72) Inventors: Masami Kawagishi, Kawasaki (JP); Daisuke Furukawa, Tokyo (JP); Bin Chen, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/093,535

(22) PCT Filed: Apr. 7, 2017

(86) PCT No.: PCT/JP2017/014514
§ 371 (c)(1),
(2) Date: Oct. 12, 2018

(87) PCT Pub. No.: WO2017/179503
PCT Pub. Date: Oct. 19, 2017

(65) Prior Publication Data
US 2019/0164283 A1   May 30, 2019

(30) Foreign Application Priority Data

Apr. 13, 2016 (JP) .............................. JP2016-080650

(51) Int. Cl.
*G06T 7/00* (2017.01)
*G16H 50/70* (2018.01)
(Continued)

(52) U.S. Cl.
CPC ............. *G06T 7/0014* (2013.01); *G06N 5/04* (2013.01); *G16H 30/40* (2018.01); *G16H 50/20* (2018.01);
(Continued)

(58) Field of Classification Search
CPC .............................. G16H 30/40; G16H 50/70
See application file for complete search history.

(56) References Cited

U.S. PATENT DOCUMENTS 9,465,978 B2 * 10/2016 Hachisuka .............. A61B 5/165
9,693,706 B2 * 7/2017 Shiodera ................ A61B 5/055
(Continued)

FOREIGN PATENT DOCUMENTS

CN 102722633 A 10/2012
CN 111368708 A * 7/2020
(Continued)

*Primary Examiner* — Charles T Shedrick
(74) *Attorney, Agent, or Firm* — Canon U.S.A., Inc. IP Division

(57) ABSTRACT

The present invention is to provide an apparatus presenting information serving as a reason for inference as information on findings so as to be easily recognized by a doctor. A medical diagnosis support apparatus infers a diagnostic name derived from a medical image based on image feature values indicating features of a region included in the medical image, acquires information on findings representing the features of the region included in the medical image based on the image feature values, and presents the information on the findings as a reason for the inference.

26 Claims, 7 Drawing Sheets

(51) Int. Cl.
*G16H 50/20* (2018.01)
*G16H 30/40* (2018.01)
*G06N 5/04* (2006.01)

(52) U.S. Cl.
CPC ... *G16H 50/70* (2018.01); *G06T 2207/30004* (2013.01)

(56) References Cited

U.S. PATENT DOCUMENTS

| | | | |
|---|---|---|---|
| 10,140,421 B1* | 11/2018 | Bernard | G06F 40/279 |
| 10,824,908 B1* | 11/2020 | Park | G06T 7/70 |
| 10,878,948 B2* | 12/2020 | Lyman | G06F 21/6254 |
| 2002/0065460 A1 | 5/2002 | Murao | |
| 2011/0161278 A1* | 6/2011 | Kawagishi | G16H 50/20 706/52 |
| 2012/0054652 A1* | 3/2012 | Kawagishi | G16H 50/20 715/764 |
| 2012/0136882 A1* | 5/2012 | Kawagishi | G06F 16/26 707/758 |
| 2012/0254101 A1* | 10/2012 | Kawagishi | G16H 50/70 706/52 |
| 2013/0096941 A1* | 4/2013 | Kanada | G16H 10/20 705/2 |
| 2013/0294676 A1* | 11/2013 | Parvin | G16B 20/00 382/133 |
| 2014/0142413 A1 | 5/2014 | Chang | |
| 2015/0019473 A1 | 1/2015 | Yakami | |
| 2018/0144244 A1* | 5/2018 | Masoud | G06N 3/0454 |
| 2018/0218514 A1* | 8/2018 | Berger | G06T 11/008 |
| 2018/0330500 A1* | 11/2018 | Sakurai | G16H 30/40 |
| 2018/0350470 A1* | 12/2018 | Kawagishi | G16H 30/40 |
| 2019/0005644 A1* | 1/2019 | Yaguchi | G06K 9/56 |
| 2019/0027252 A1* | 1/2019 | Calhoun | G06K 9/6247 |
| 2019/0148006 A1* | 5/2019 | Ahmed | A61B 5/0013 705/2 |
| 2019/0148015 A1* | 5/2019 | Futamura | G16H 50/70 705/2 |
| 2019/0156947 A1* | 5/2019 | Nakamura | G16H 50/20 |
| 2019/0164283 A1* | 5/2019 | Kawagishi | G16H 30/40 |
| 2019/0282214 A1* | 9/2019 | Park | G06T 7/11 |
| 2020/0005942 A1* | 1/2020 | Kawagishi | G06T 7/0016 |
| 2020/0105414 A1* | 4/2020 | Kikuchi | G16H 50/20 |
| 2020/0210767 A1* | 7/2020 | Do | G06N 3/08 |
| 2020/0211692 A1* | 7/2020 | Kalafut | G16H 30/20 |
| 2020/0320709 A1* | 10/2020 | Geipel | G06K 9/6256 |
| 2021/0027465 A1* | 1/2021 | Kawagishi | G06T 7/0012 |
| 2021/0158936 A1* | 5/2021 | Rao | G06T 7/33 |

FOREIGN PATENT DOCUMENTS

| | | | | |
|---|---|---|---|---|
| CN | 111655116 A | * | 9/2020 | A61B 1/045 |
| CN | 111696642 A | * | 9/2020 | G16H 30/40 |
| EP | 2213224 A1 | * | 8/2010 | G06T 7/0012 |
| EP | 2402903 A1 | | 1/2012 | |
| EP | 2506173 A1 | | 10/2012 | |
| EP | 2551822 A2 | * | 1/2013 | G16H 40/63 |
| EP | 3151142 A1 | * | 4/2017 | G16H 70/60 |
| EP | 3293736 A1 | * | 3/2018 | G06K 9/4671 |
| JP | 2006-043007 A | | 2/2006 | |
| JP | 2010082001 A | | 4/2010 | |
| JP | 2012249964 A | | 12/2012 | |
| JP | 2014-29644 A | | 2/2014 | |
| JP | 2014-048798 A | | 3/2014 | |
| JP | 5744631 B2 | * | 7/2015 | |
| JP | 5816321 B2 | * | 11/2015 | |
| JP | 2017191469 A | * | 10/2017 | G16H 30/40 |
| WO | 2014184887 A1 | | 11/2014 | |
| WO | WO-2017137070 A1 | * | 8/2017 | G03B 17/565 |
| WO | WO-2017179503 A1 | * | 10/2017 | G16H 50/70 |
| WO | WO-2019107177 A1 | * | 6/2019 | G06T 7/0012 |

* cited by examiner

FIG. 4

| n | $F_n$ | nk | $f_{nk}$ |
|---|---|---|---|
| 1 | SHAPE | 11 | SPHERICAL |
| | | 12 | LOBULATED |
| | | 13 | POLYGON |
| | | 14 | IRREGULAR |
| 2 | CUTTING | 21 | DEEP |
| | | 22 | SHALLOW |
| | | 23 | NON |
| 3 | SERRATED PERIPHERY | 31 | SHARP |
| | | 32 | BLUNT |
| | | 33 | NON |
| ... | | | |
| N | INVOLVEMENT OF BRONCHUS | N1 | POSITIVE |
| | | N2 | SUSPECTED |
| | | N3 | NEGATIVE |

| j | $C_j$ | jk | $c_{jk}$ |
|---|---|---|---|
| 1 | FEVER | 11 | POSITIVE |
| | | 12 | NEGATIVE |
| 2 | COUGHING | 21 | POSITIVE |
| | | 22 | NEGATIVE |
| 3 | BLOODY SPUTUM | 31 | POSITIVE |
| | | 32 | NEGATIVE |
| ... | | | |
| J | CEA | | <CONTINUOUS VALUE $c_J$> |

FIG. 5

| $e_v$ | $I(e_v)$ |
|---|---|
| $i_1$ | 0.21 |
| $i_2$ | −0.16 |
| $i_3$ | 0.15 |
| ... | |
| $i_M$ | 0.02 |
| $c_{11}$ | −0.13 |
| ... | |
| $c_J$ | 0.16 |

MEDICAL DIAGNOSIS SUPPORT APPARATUS, INFORMATION PROCESSING METHOD, MEDICAL DIAGNOSIS SUPPORT SYSTEM, AND PROGRAM

TECHNICAL FIELD

The present invention relates to a medical diagnosis support apparatus, an information processing method, a medical diagnosis support system, and a program.

BACKGROUND ART

In recent years, various types of medical information are used in diagnosis and a technique of a system has been highly expected in which a result acquired by a computer analyzing medical information including medical images is used as support for diagnosis. PTL 1 discloses presentation of a result of search associated with a radiogram interpretation item used in the search in a system in which a similar case is searched for based on image feature values acquired by analyzing a medical image and the radiogram interpretation item of a past case.

Even in a case where only a result of analysis is displayed when the result obtained by a computer analyzing medical information is used by a doctor as support for diagnosis, the doctor may not determine whether the result is useful. A determination as to whether a past case deeply associated with a radiogram interpretation item used in the search is useful information for the diagnosis to be made may not be reliably made only by displaying the past case.

CITATION LIST

Patent Literature

PTL 1: Japanese Patent Laid-Open No. 2014-29644

SUMMARY OF INVENTION

According to some embodiments of the present invention, a medical diagnosis support apparatus includes an inference unit configured to infer a diagnostic name derived from a medical image based on image feature values indicating features of a region included in the medical image, an acquisition unit configured to acquire information on findings representing the features of the region included in the medical image based on the image feature values, and a presentation control unit configured to present the information on the findings acquired by the acquisition unit as a reason for the inference performed by the inference unit.

Further features of the present invention will become apparent from the following description of exemplary embodiments with reference to the attached drawings.

BRIEF DESCRIPTION OF DRAWINGS

FIG. 4 is a diagram illustrating information acquired by the medical diagnosis support apparatus according to the embodiment of the present invention.

FIG. 5 is a diagram illustrating information acquired by the medical diagnosis support apparatus according to the embodiment of the present invention.

DESCRIPTION OF EMBODIMENTS

Figure 1:
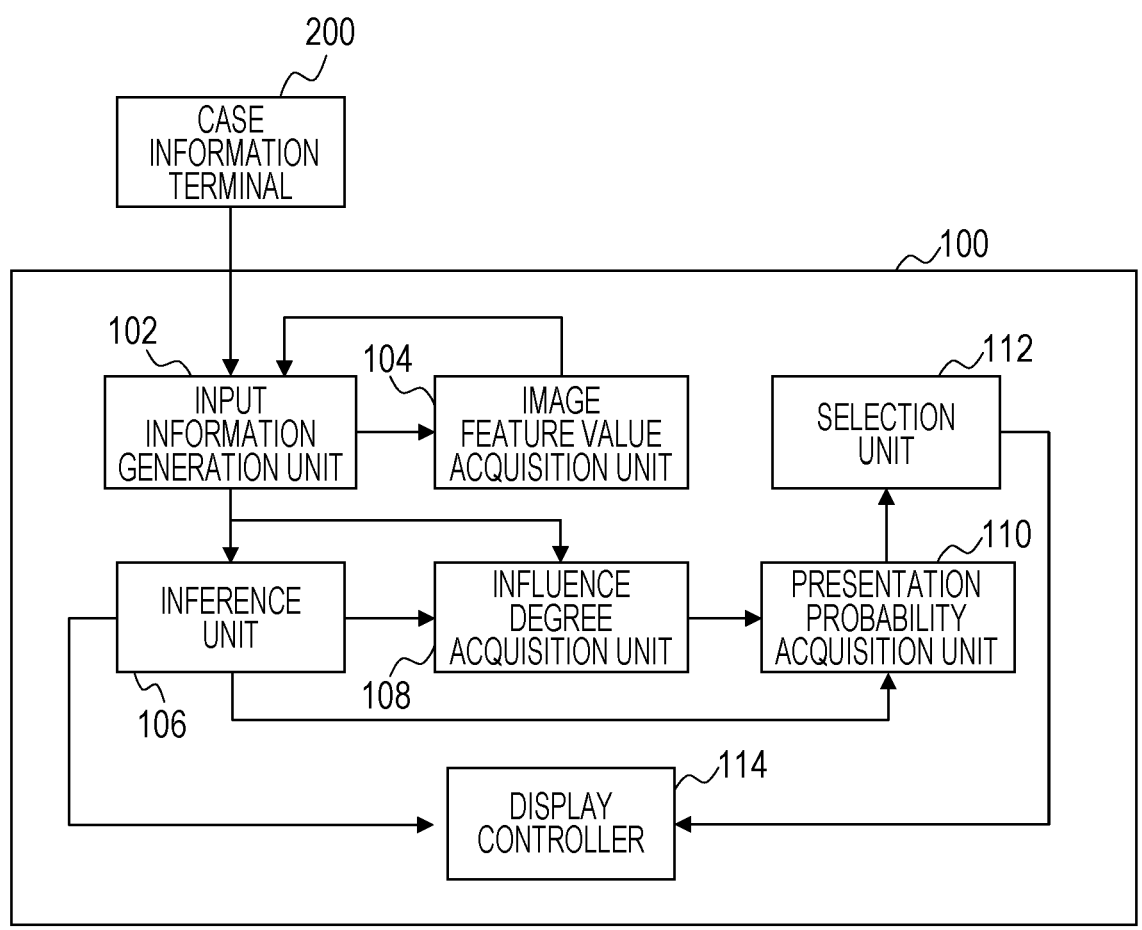
FIG. 1 is a diagram illustrating a functional configuration of a medical diagnosis support apparatus according to an embodiment of the present invention.

Hereinafter, embodiments of the present invention will be described with reference to the accompanying drawings.

First Embodiment

In a medical field, an image diagnosis is performed based on a medical image acquired by an imaging apparatus, such as an X-ray computer tomography (CT) apparatus or a magnetic resonance imaging (MRI) apparatus. Here, drawing of a diagnosis by observing a medical image is referred to as "radiogram interpretation". In the image diagnosis, a radiogram interpretation doctor specialized in the image diagnosis performs the radiogram interpretation in response to a request for performing radiogram interpretation from a doctor in charge, for example. The radiogram interpretation doctor specifies a lesion rendered in a medical image and a symptom of a patient who is an examiner by a comprehensive determination in accordance with findings acquired from the image (hereinafter referred to as "image findings") and various measurement values. The radiogram interpretation doctor describes a background which leads to the diagnosis using the image findings and the measurement values in a radiogram interpretation report for the doctor in charge who is a requester.

To support the radiogram interpretation, a system which presents a result acquired when a computer analyzes medical information has been proposed. It is preferable that information serving as a reason for the result is presented before the doctor uses the result of the analysis. However, in a case where information input in the analysis (hereinafter referred to as "input information") is acquired by digitalizing a feature rendered in an image, such as an image feature value, even if information which considerably affects the result is identified and presented, the information is difficult to understand for a user. A medical diagnosis support apparatus according to a first embodiment of the present invention presents information (hereinafter referred to as "reference information") which is instinctively understandable and which serves as a clue for deriving an inference result even when input information includes information which is difficult to understand for the user, such as an image feature value. Examples of the reference information which is instinctively understandable by the user include information on findings representing features of a lesion region by a language, for example.

A detailed description will be made hereinafter. A medical diagnosis support apparatus 100 according to the first embodiment acquires a medical image which is a target of the radiogram interpretation and information included in an electronic health record and the like, and presents information serving as a clue of a diagnosis (reference information) so as to perform diagnosis support.

Hereinafter, the medical diagnosis support apparatus 100 acquires a medical image associated with radiogram interpretation of an abnormal shadow of a lung, information attached to the medical image, and information acquired when a medical examination is performed (hereinafter referred to as "clinical information"), such as, a past medical history and a value of a blood test including a tumor maker. A case where input information is generated based on the acquired information, information serving as a clue of a diagnosis is generated using the input information in a format understandable by a user (a doctor), and the information is presented will be described as an example. The present invention is not limited to this case and diagnostic names, image feature values, image findings, clinical information, and the like are merely examples for describing steps of a process performed by the medical diagnosis support apparatus.

FIG. 1 is a diagram illustrating a functional configuration of the medical diagnosis support apparatus 100. The medical diagnosis support apparatus 100 is connected to a case information terminal 200 in a communication available manner. The medical diagnosis support apparatus 100 includes an input information generation unit 102, an image feature value acquisition unit 104, an inference unit 106, an influence degree acquisition unit 108, a presentation probability acquisition unit 110, a selection unit 112, and a display controller 114. The functional components included in the medical diagnosis support apparatus 100 are connected to one another through an internal bus or the like.

The case information terminal 200 acquires information on a case to be subjected to a diagnosis from a server (not illustrated). The information on a case includes a medical image or medical information, such as clinical information described in an electronic health record. The case information terminal 200 may be connected to an external storage device (not illustrated), such as a floppy disk drive (FDD), a hard disk drive (HDD), a compact disk (CD) drive, a digital versatile disk (DVD) drive, a magneto-optical (MO) disc drive, or a Zip drive so as to acquire medical information from the external storage device.

The case information terminal 200 may display the medical information in a monitor 1005 through the display controller 114 in a format in which a user may perform the radiogram interpretation. Specifically, the case information terminal 200 provides a graphic user interface (GUI) to be used by the user to input coordinate information of a region which is seen by the user to include an abnormal shadow in a medical image displayed in the monitor 1005 through the display controller 114. Alternatively, the case information terminal 200 may provide a GUI to be used by the user to input image findings of the region in the medical image displayed in the monitor 1005 through the display controller 114. The case information terminal 200 acquires information input by the user through the GUI as information attached to the medical image (hereinafter referred to as "supplemental information").

The case information terminal 200 transmits the medical image, medical information, such as clinical information, and the supplemental information to the medical diagnosis support apparatus 100 through a network or the like.

The input information generation unit 102 generates input information based on the information transmitted from the case information terminal 200 to the medical diagnosis support apparatus 100, such as the medical image, the clinical information, and the supplemental information. The input information is aggregate of elements of information to be input for inference performed by the inference unit 106.

In the first embodiment, the input information generation unit 102 outputs the medical image and the supplemental information to the image feature value acquisition unit 104 and acquires image feature values supplied from the image feature value acquisition unit 104 in response to the output. Then the input information generation unit 102 outputs the acquired image feature values and the clinical information as the input information to the inference unit 106 and the influence degree acquisition unit 108.

The image feature value acquisition unit 104 acquires image feature values in accordance with the medical image and the supplemental information output from the input Information generation unit 102. The image feature value acquisition unit 104 performs image processing on the medical image to be subjected to the radiogram interpretation so as to acquire image feature values of the medical image. In a case where the input information generation unit 102 outputs the supplemental information, such as coordinate information indicating an abnormal region, the image feature value acquisition unit 104 acquires image feature values of the abnormal region indicated by the coordinate information. Here, the image feature values are numerical values indicating features of an image. Specifically, the image feature values indicate a shape, a density, or a size of the abnormal region, for example. The image feature value acquisition unit 104 outputs the acquired image feature values to the input information generation unit 102.

The inference unit 106 infers a diagnostic name of a target case using the input information generated by the input information generation unit 102 as an input. In the first embodiment, an inference of a diagnostic name associated with an abnormal shadow of a lung will be described as an example. The inference unit 106 may acquire a position of the abnormal shadow in accordance with the supplemental information output from the input information generation unit 102 or image processing. The inference unit 106 acquires a probability that the abnormal shadow in the medical image corresponds to a specific diagnostic name as an inference result. The inference unit 106 outputs the acquired inference result to the influence degree acquisition unit 108 and the display controller 114. The inference unit 106 is an example of an inference unit.

The influence degree acquisition unit 108 acquires degrees of influence of the elements included in the input information to the inference result using the input information generated by the input information generation unit 102 and the inference result output from the inference unit 106. The influence degree acquisition unit 108 outputs the acquired influence degrees of the elements to the presentation probability acquisition unit 110.

The presentation probability acquisition unit 110 acquires probabilities of presentation of information which is candidates of the reference information using the influence degrees acquired by the influence degree acquisition unit 108. The reference information is presented for the user by the display controller 114 as a reason for the inference performed by the inference unit 106. The presentation probabilities are indices indicating preferred degrees of presentation as the reference information of the candidates of the reference information. The presentation probability acquisition unit 110 acquires image findings based on the image feature values. The image findings and the clinical information in the input information are the candidates of the reference information. The presentation probability acquisition unit 110 outputs the acquired presentation probabilities of the candidates of the reference information to the selection unit 112. The presentation probability acquisition unit 110 is an example of an acquisition unit.

The selection unit 112 selects the reference information, that is, information presented as the reason for the inference, based on the presentation probabilities of the candidates of the reference information acquired by the presentation probability acquisition unit 110. The selection unit 112 outputs the selected information to the display controller 114. The selection unit 112 is an example of a selection unit.

The display controller 114 presents the inference result output from the inference unit 106 and the reference information selected by the selection unit 112 to the user. The display controller 114 controls content to be displayed in the monitor 1005 in accordance with the inference result and the reference information.

Note that at least some of the components included in the medical diagnosis support apparatus 100 of FIG. 1 may be realized as independent apparatuses. Furthermore, at least some of the components may be realized as software which realizes individual functions. In the first embodiment, the units are individually realized by software.

Figure 2:
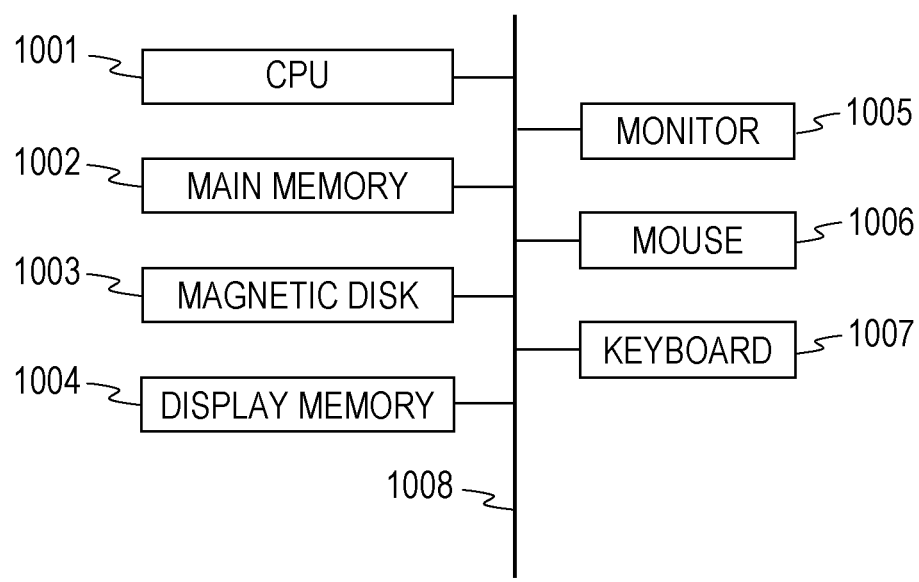
FIG. 2 is a diagram illustrating a hardware configuration of the medical diagnosis support apparatus according to the embodiment of the present invention.

FIG. 2 is a diagram illustrating a hardware configuration of the medical diagnosis support apparatus 100. A CPU 1001 mainly controls operations of individual components. A main memory 1002 stores control programs to be executed by the CPU 1001 and provides a working area for execution of the programs performed by the CPU 1001. A magnetic disk 1003 stores an operating system (OS), device drivers of peripherals, and programs which realize various application software including programs for performing a process described below. The functions (software) of the medical diagnosis support apparatus 100 of FIG. 1 and the process in a flowchart described below are realized when the CPU 1001 executes the programs stored in the main memory 1002 and the magnetic disk 1003.

A display memory 1004 temporarily stores data to be displayed in the monitor 1005, for example. The monitor 1005 is a CRT monitor or a liquid crystal monitor which displays images, text, and the like based on the data supplied from the display memory 1004. A mouse 1006 and a keyboard 1007 are used by the user to perform pointing input and input of text, respectively.

The components described above are connected to one another through a common bus 1008 in a communication available manner. The CPU 1001 is an example of a processor. The medical diagnosis support apparatus 100 may include a plurality of processors. The medical diagnosis support apparatus 100 may include a graphics processing unit (GPU) used to dedicatedly perform the process of the inference unit 106 or a field-programmable gate array (FPGA) which programs the functions of the inference unit 106. Furthermore, the main memory 1002, the magnetic disk 1003, and the display memory 1004 are examples of a memory.

Figure 3:
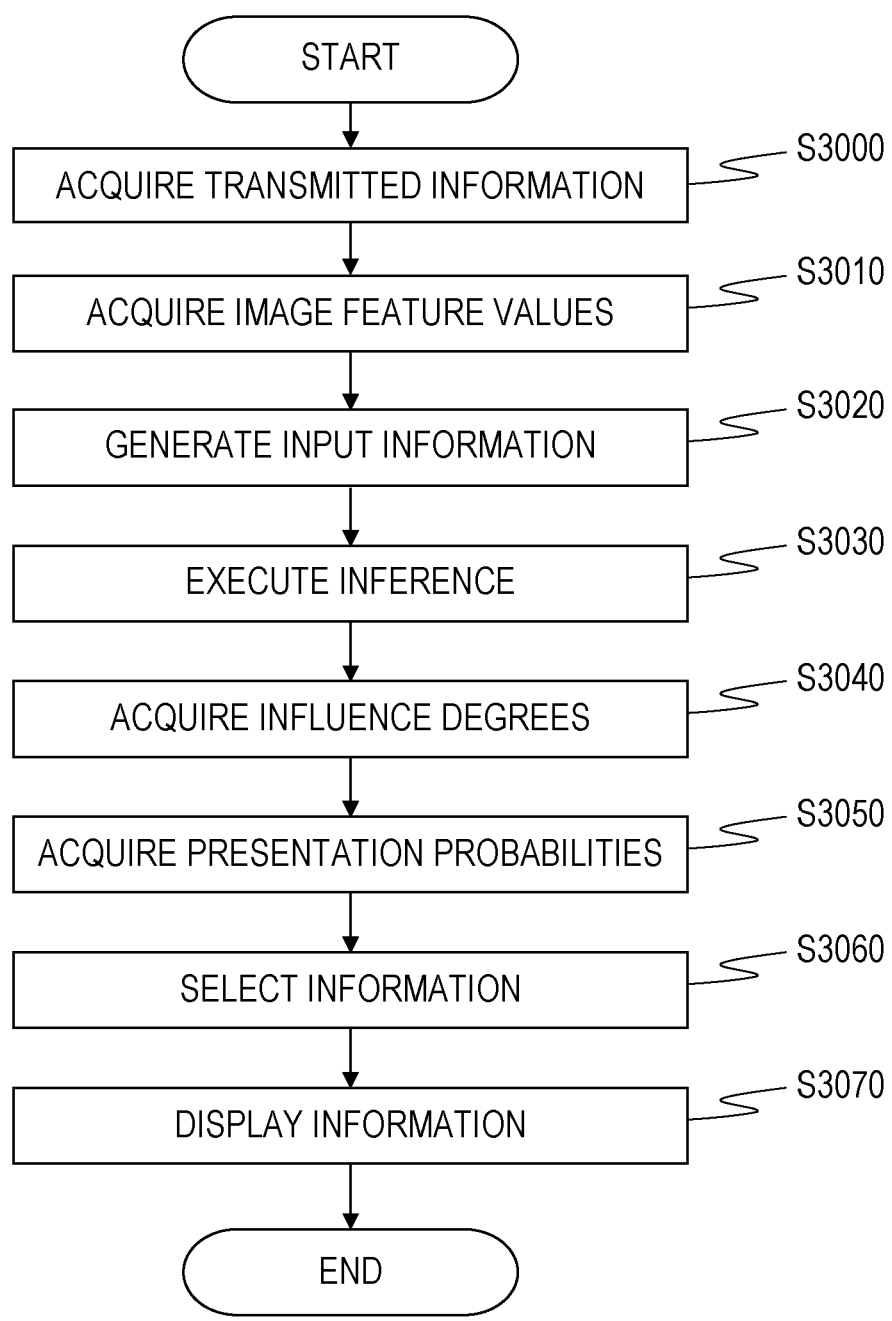
FIG. 3 is a flowchart of a process performed by the medical diagnosis support apparatus according to the embodiment of the present invention.

FIG. 3 is a flowchart of the process performed by the medical diagnosis support apparatus 100. In a description below, image feature values are denoted by "$I_m$" (m=1 to M), image findings are denoted by "$F_n$" (n=1 to N), and clinical information is denoted by "$C_j$" (j=1 to J). Here, elements of the values $I_m$ are continuous values, elements of the values $F_n$ are discrete values (category values), and elements of the values $C_j$ are continuous values or discrete values depending on the elements. When the values are discrete values, the discrete values are represented by "$f_{nk}$" and "$c_{jk}$". Note that the value k varies depending on the values $F_n$ and $C_j$.

Furthermore, when the image feature values $I_m$ and the clinical information $C_j$ are continuous values, the values are represented by "$i_m$" and "$c_j$".

In the first embodiment, items and values illustrated in FIG. 4 are used as the image findings and the clinical information. For example, in a case of image findings, one of four values $f_{11}$ "spherical", $f_{12}$ "lobulated", $f_{13}$ "polygon", and $f_{14}$ "irregular" is selected in an item $F_1$ "shape". One of three values $f_{21}$ "deep", $f_{22}$ "shallow" and $f_{23}$ "non" is selected in an item $F_2$ "cutting". One of two values $c_{11}$ "positive" and $c_{12}$ "negative" is selected in an item $C_1$ "fever" in the clinical information. A continuous value $c_J$ is selected as an element in an item $C_J$ of "CEA" (a type of tumor marker).

In a description below, aggregate of values $I_m$, $F_n$, and $C_j$ as elements is denoted by "E" and the input information is denoted by "$E_f$". Furthermore, a diagnostic name is denoted by "D" in the description below. In the first embodiment, the inference unit 106 infers a diagnostic name associated with the abnormal shadow of the lung by selecting one of three values corresponding to a primary lung cancer, a lung metastatic cancer, and others. Hereinafter, the primary lung cancer, the lung metastatic cancer, and the others are denoted by "$d_1$", "$d_2$", and "$d_3$", respectively. Furthermore, an inference probability of a diagnostic name $d_s$ (s=1, 2, or 3) acquired when the input information $E_f$ is input to the inference unit 106 is denoted by "$P(d_s|E_f)$".

In step S3000, the input information generation unit 102 acquires information (a medical image, clinical information, and supplemental information) transmitted from the case information terminal 200 to the medical diagnosis support apparatus 100. In the first embodiment, a case where only coordinate information of an abnormal shadow is transmitted as the supplemental information will be described as an example.

In step S3010, the image feature value acquisition unit 104 performs image processing based on the medical image and the supplemental information supplied in step S3000 so as to acquire image feature values. The image feature values acquired in this step may be general image feature values, such as an average value or dispersion of density (luminance) in a processing target region in the image or image feature values based on a filter output.

In the first embodiment, the image feature value acquisition unit 104 refers to the supplemental information (the coordinate information of the abnormal shadow) acquired in step S3000, segments a region of the abnormal shadow from the medical image, and thereafter, image feature values are acquired through the image processing.

In step S3020, the input information generation unit 102 generates input information based on the clinical information acquired in step S3000 and the image feature values acquired in step S3010. For example, it is assumed here that the clinical information acquired in step S3000 is $\{c_{12}, c_{22}, \ldots, c_J\}$ and the image feature values acquired in step S3010 are $\{i_1, i_2, \ldots, i_M\}$. In this case, the input information $E_f$ is represented as follows: $E_f=\{c_{12}, c_{22}, \ldots c_J, i_1, i_2, \ldots, i_M\}$.

In step S3030, the inference unit 106 executes inference associated with the abnormal shadow of the lung which is the diagnostic target based on the input information generated in step S3020. Specifically, the inference unit 106 infers a diagnostic name derived from the medical image in accordance with the image feature values which represent features of the region included in the medical image. Specifically, values $P(d_s|E_f)$ are acquired. Examples of an inference method include a method using a Bayesian network, a method using a support vector machine, and a method using a neural network. In the first embodiment, the Bayesian network is used.

In step S3040, the influence degree acquisition unit 108 acquires degrees of influence of the elements included in the input information to an inference result using the input information generated in step S3020 and a result of the inference executed in step S3030. Specifically, the influence degree acquisition unit 108 acquires influence degrees which are degrees of influence to the inference of the diagnostic name for the individual information used as the input for the inference performed by the inference unit 106. In the first embodiment, degrees of influence to a diagnostic name $d_f$ having the highest inference probability among various diagnostic names are acquired. Specifically, an influence degree of a certain element $e_v$ ($e_v$ is an element included in $E_f$) is acquired by subtracting an inference probability of the diagnostic name $d_f$ acquired when only the element $e_v$ is removed from the input information $E_f$ from an inference probability of the diagnostic name $d_f$ inferred using the input information $E_f$. The influence degree of the element is denoted by "$I(e_v)$" and defined as Expression 1 below.

$$I(e_v)=P(d_f|E_f)-P(d_f|E_f-e_v) \qquad (1)$$

When the value "$I(e_v)$" is positive, since the element $e_v$ is not included in the input information, the inference probability of the diagnostic name $d_f$ is reduced. Accordingly, the element $e_v$ is seen to be information which affirms the diagnostic name $d_f$. On the other hand, when the value "$I(e_v)$" is negative, since the element $e_v$ is not included in the input information, the inference probability of the diagnostic name $d_f$ is increased. Accordingly, element $e_v$ is information which disaffirms the diagnostic name $d_f$.

In step S3050, the presentation probability acquisition unit 110 acquires presentation probabilities of the candidates of the reference information, that is, information to be presented as the reason for the inference. Presentation probabilities of the elements including the image findings and the clinical information are represented by absolute values of the influence degrees acquired in step S3040. Furthermore, the presentation probability acquisition unit 110 acquires the presentation probabilities of the elements of the image feature values in accordance with the relationships between the image feature values and the image findings.

In the first embodiment, the presentation probability acquisition unit 110 searches for a similar case in accordance with the image feature values and converts the image feature values into image findings having presentation probabilities attached thereto using the information on findings associated with the similar case. The similar case may be retrieved from a database of cases stored in the case information terminal 200 or a database of cases stored in a server (not illustrated) installed outside the medical diagnosis support apparatus 100. It is assumed that image findings are assigned in advance to the individual cases stored in the case information terminal 200 or the external server (not illustrated). Specifically, the presentation probability acquisition unit 110 acquires an image finding based on the image feature values. More specifically, the presentation probability acquisition unit 110 acquires information on findings associated with the image feature values included in the input information input to the inference unit 106.

Specifically, the presentation probability acquisition unit 110 extracts a plurality of cases having similarity degrees attached thereto by performing weighting similarity case search using absolute values of the influence degrees of the image feature values as weights. Then a presentation probability is acquired based on similarity degrees between the image findings assigned to the extracted case (a target case) and the image feature values of the case to be subjected to diagnosis support performed by the medical diagnosis support apparatus 100 (a current case). Specifically, the target case is an example of a similar case having image feature values similar to the image feature values included in the input information input to the inference unit 106.

First, the presentation probability acquisition unit 110 acquires similarity degrees as described below. Values of image feature values $i_m$ of target cases ($T_x$: x=1 to X) are represented by $i_{rm}$, and similarity degrees $Sim(T_x)$ between a current case and the target cases $T_x$ are represented by Expression 2 below. Note that the image feature values are normalized to 0 or 1. The similarity degree $Sim(T_x)$ in Expression 2 has a value nearer to 1 as the image feature value of the current case and the image feature value of the target case $T_x$ are closer to each other.

[Math. 1]

$$Sim(T_x) = 1 - \frac{\sum_{m=1}^{M}\left(|I(i_m)|\sqrt{(i_m - i_{T_xm})^2}\right)}{\sum_{m=1}^{M}|I(i_m)|} \qquad (2)$$

Note that the presentation probability acquisition unit 110 may acquire a similarity degree by another method. The presentation probability acquisition unit 110 may not use the influence degree as a weight, for example, but may use a Mahalanobis' generalized distance between S and $T_x$ as the similarity degree. In this case, conversion is preferably performed such that a similarity degree of 1 is acquired when the Mahalanobis generalized distance is 0.

Furthermore, the presentation probability acquisition unit 110 acquires presentation probabilities ($Pre(f_{nk})$) of the values of the image findings as illustrated in Expression 3 in accordance with the similarity degrees and the image findings assigned to the target case.

[Math. 2]

$$Pre(f_{nk}) = \frac{1}{X}\sum_{x=1}^{X}(Sim(T_x) \cdot \delta_x(f_{nk})) \qquad (3)$$

Expression 3 illustrates a function in which $\delta_x(f_{nk})$ is 1 when values $f_{nk}$ of the image findings are assigned to the target cases $T_x$ whereas $\delta_x(f_{nk})$ is 0 when the values $f_{nk}$ are not assigned to the target cases $T_x$. In Expression 3, the larger the number of values of the common image finding in a group of target cases having high similarity degrees is, the larger the presentation probability of the value of the image finding is. Specifically, the presentation probability acquisition unit 110 acquires the presentation probability in accordance with the similarity degree and statistical information indicating frequency of association with a certain image finding in the target case group. Furthermore, the image feature values are converted into image findings having presentation probabilities attached thereto.

In the foregoing embodiment, the presentation probability acquisition unit 110 acquires the presentation probabilities using all data (X cases) included in the database which stores similar cases. However, the present invention is not limited to this, and the presentation probability acquisition unit 110 may acquire the presentation probabilities only using cases ranked in top X' of the similarity degrees or only using X' cases having similarity degrees which are larger than a threshold value which is set in advance.

In step S3060, the selection unit 112 selects information to be presented as a reason for the inference based on the presentation probabilities acquired in step S3050. The selection unit 112 selects information to be presented as the reason for the inference from the elements except for the image feature values in the input information input to the inference unit 106 and the image findings acquired in step S3050. The information selected by the selection unit 112 is presented as the reference information, that is, the reason for the inference. Specifically, the selection unit 112 selects the information to be presented as the reason for the inference in accordance with the similarity degrees between the image feature values included in the input information input to the inference unit 106 and the image feature values of the similar cases and the presentation probabilities based on the statistical information indicating the frequency of the association between the similar cases and the image findings.

In the first embodiment, three information items are selected in a descending order of the presentation probabilities. Note that, if a plurality of values ($f_{n1}$ and $f_{n2}$, for example) may be acquired for an item ($F_n$, for example) of one image finding, only one of the values corresponding to a higher presentation probability is selected and the others are ignored. The number of selections and a selection method are not limited to these. The number of selections may be other than 3. The method for selecting information which satisfies a predetermined threshold value may be employed.

In step S3070, the display controller 114 controls display content in accordance with the inference result acquired in step S3030 and the information selected in step S3060. Specifically, the display controller 114 presents the information which indicates findings representing features of the region included in the medical image of the case which is the target of the diagnosis support and which is selected by the selection unit 112 as the reason for the inference.

Figure 6:
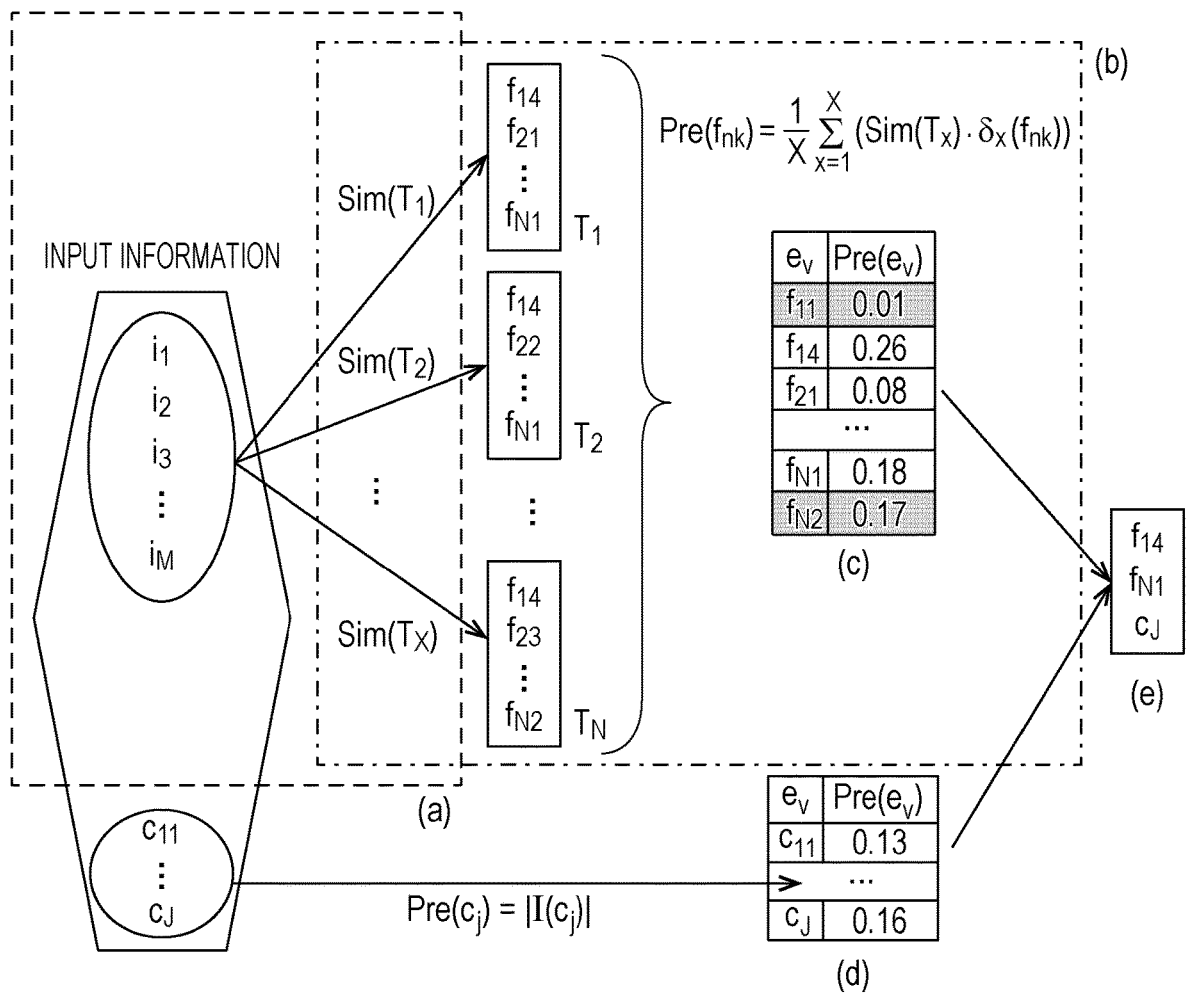
FIG. 6 is a diagram illustrating information acquired by the medical diagnosis support apparatus according to the embodiment of the present invention.

Hereinafter, the flow from step S3040 to step S3070 will be described with reference to FIGS. 5 to 7. It is assumed here that the influence degree acquisition unit 108 acquires influence degrees, as illustrated in FIG. 5, of the elements of the input information input to the inference unit 106 in step S3040. In step S3050, the presentation probability acquisition unit 110 acquires similarity degrees between image feature values $i_1$ to $i_m$ illustrated in (a) of FIG. 6 in the input information and the target cases in accordance with Expression 2. Thereafter, the presentation probability acquisition unit 110 acquires presentation probabilities in accordance with Expression 3 using the degrees of similarity to the target cases and the image findings associated with and the target cases as illustrated in (b) of FIG. 6. By this, the image feature values included in the input information are converted into values of the image findings having the presentation probabilities attached thereto. Specifically, the presentation probability acquisition unit 110 converts M image feature values into values of Y image findings having the presentation probabilities attached thereto. Consequently, the presentation probability acquisition unit 110 acquires image findings having the presentation probabilities attached thereto as illustrated in (c) of FIG. 6. Furthermore, the presentation probability acquisition unit 110 acquires absolute values of the influence degrees of the clinical information in the input information as presentation probabilities. Consequently, the presentation probability acquisition unit 110 acquires clinical information having the presentation probabilities attached thereto as illustrated in (d) of FIG. 6. Note that, since all cases stored in the database, not illustrated, are used in this embodiment, Y is a fixed number irrespective of the image feature values of the current case. On the other hand, the value Y may be changed in a case cases are limited to top X' cases or X" cases which exceed a threshold value.

Subsequently, in step S3060, information is selected in accordance with the image findings and the presentation probabilities of the elements of the clinical information. In the example of FIG. 6, the values of the elements are arranged in descending order of the presentation probabilities as follows: $f_{14}$, $f_{N1}$, $f_{N2}$, $c_1$, and so on. However, $f_{N1}$ and $f_{N2}$ are both values of $F_N$, and therefore, only $f_{N1}$ having a higher presentation probability is taken into consideration but $f_{N2}$ is excepted. Accordingly, $f_{14}$, $f_{N1}$, and $c_1$ are finally selected as the reference information, that is, the reason for the inference as illustrated in (e) of FIG. 6. That is, in the case where different values are included in findings representing the same feature in the candidates of the reference information, the selection unit 112 selects information associated with a value of the finding having the higher presentation probability as the reference information or the reason for the inference.

Figure 7:
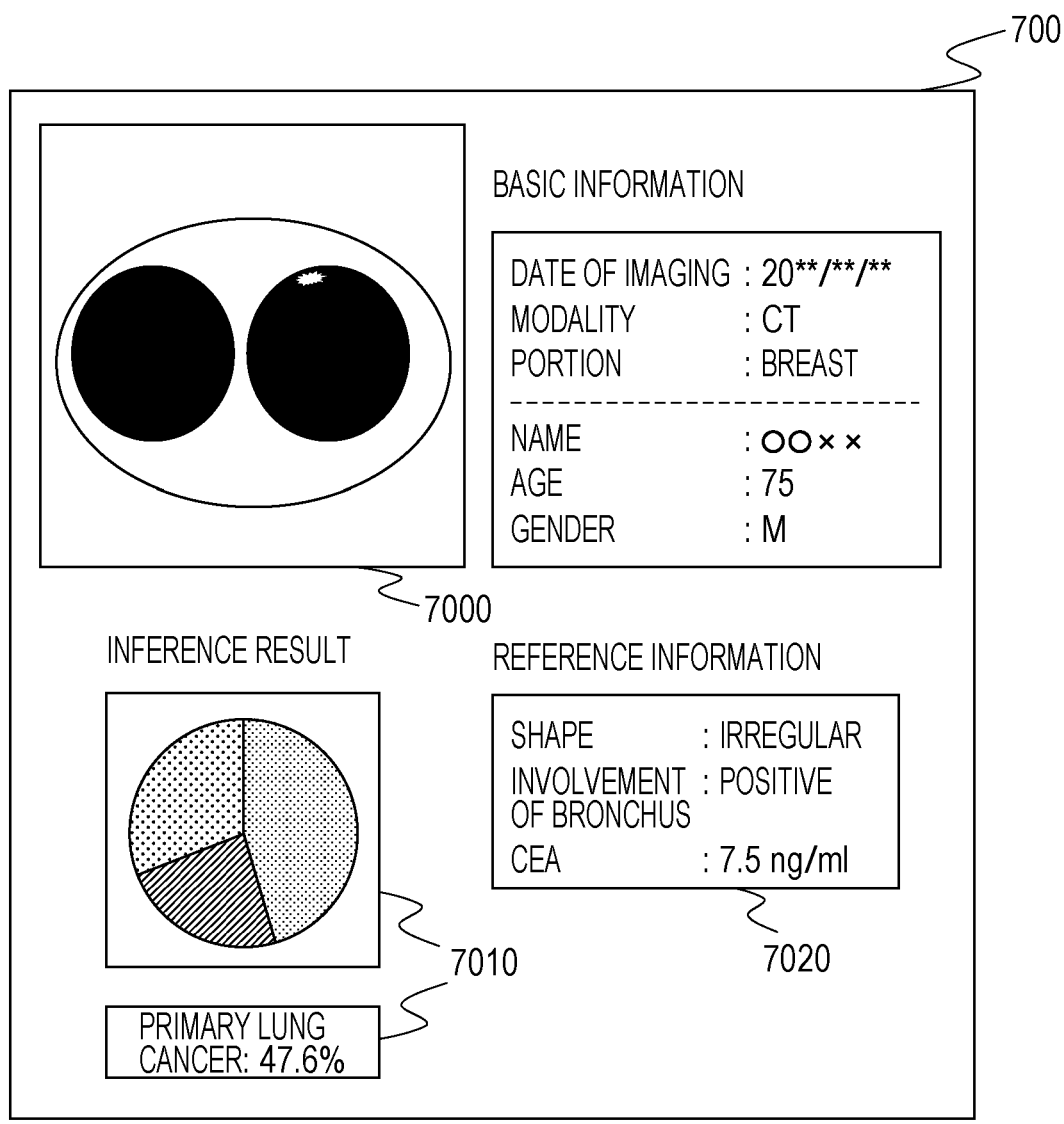
FIG. 7 is a diagram illustrating a screen displayed by the medical diagnosis support apparatus according to the embodiment of the present invention.

FIG. 7 is a diagram illustrating a screen displayed in the monitor 1005 under control of the display controller 114 in step S3070. Display content 700 includes a medical image 7000 acquired in step S3000, an inference result 7010 acquired in step S3030, and reference information 7020 selected in step S3060. The user may use the inference result 7010 and the reference information 7020 as support information at a time of image diagnosis.

According to the first embodiment, the medical diagnosis support apparatus 100 performs inference based on the input information of the medical image and acquires degrees of influence of the elements of the input information to the inference result. Furthermore, the medical diagnosis support apparatus 100 acquires presentation probabilities using the influence degrees of the elements. In particular, when image feature values are included in the input information, the image feature values are converted into image findings having a presentation probabilities assigned thereto and the image findings and clinical Information serving as the reference information are presented in accordance with the presentation probabilities. By this, a doctor, that is, the user, may recognize information which is the reason for the inference in a form of an image finding or clinical information which is easily understandable by human beings.

First Modification of First Embodiment

In the first embodiment, similar cases are searched for in step S3050 and image feature values are converted into image findings. The present invention is not limited to this, and image feature values may be converted into image findings having presentation probabilities attached thereto by inferring likelihood of values of the image findings using the image feature values. Here, only image feature values having influence degrees equal to or larger than a certain threshold value may be used. In this case, the other image feature values may be determined as defective values. Furthermore, only image feature values having top N influence degrees may be used. The likelihood of the image findings may be used as the presentation probabilities, or an average value, a maximum value, and a minimum value of the influence degrees of the image feature values may be integrated.

Second Modification of First Embodiment

In the first embodiment, similar cases are searched for in step S3050 and image feature values are converted into image findings. The present invention is not limited to this, and convention into image findings having presentation probabilities attached thereto may be performed using correlation ratios between image feature values and image findings. For example, the presentation probability acquisition unit 110 acquires correlation ratios $\eta_{mm}$ between image feature values $i_m$ and image findings $F_n$ of cases stored in a database and acquires an average of products of the influence degrees of the image feature values and the correlation ratios. The presentation probability acquisition unit 110 acquires presentation probabilities ($Pre(F_n)$) of the image findings $F_n$ as illustrated in Expression 4.

[Math. 3]

$$Pre(F_n) = \frac{1}{M}\sum_{m=1}^{M} \{I(i_m) \cdot \eta_{mn}\} \quad (4)$$

In another example, $F_n$ may be resolved, category values corresponding to values of K image findings which are 1 when $f_{nk}$ is detected and which are 0 when $f_{nk}$ is not detected, and correlation ratios are acquired before presentation probabilities of the values $f_{nk}$ of the image findings are acquired. Assuming that correlation ratios between the image feature values $i_m$ and the image findings $f_{nk}$ are denoted by $\eta_{mnk}$, the presentation probabilities of the value $f_{nk}$ of the image findings may be represented by Expression 5.

[Math. 4]

$$Pre(f_{nk}) = \frac{1}{M}\sum_{m=1}^{M} \{I(i_m) \cdot \eta_{mnk}\} \quad (5)$$

Specifically, a predetermined correlation ratio may be used as statistical information for representing an image feature value by a certain image finding when a presentation probability is acquired.

Second Embodiment

A medical diagnosis support apparatus 100 of a second embodiment performs inference and presentation of a reason for the inference using results of conversion from image feature values into image findings as input information for the inference.

The medical diagnosis support apparatus 100 of the second embodiment includes components the same as those of the first embodiment in FIG. 1. Note that some of functions are different from those of the first embodiment, and only portions different from those of the first embodiment will now be described.

An input information generation unit 102 generates input information based on information (an medical image, clinical information, and supplemental information) transmitted from a case information terminal 200 to the medical diagnosis support apparatus 100. In the second embodiment, the input information generation unit 102 outputs the medical image and the supplemental information to an image feature value acquisition unit 104. Thereafter, the input information generation unit 102 acquires image feature values output from the image feature value acquisition unit 104. Furthermore, the input information generation unit 102 performs inference based on the acquired image feature values and performs conversion into image findings having likelihood attached thereto. Then the input information generation unit 102 outputs the converted image findings and clinical information as input information to an influence degree acquisition unit 108 and a presentation probability acquisition unit 110. The input information generation unit 102 is an example of an acquisition unit which acquires information on findings based on image feature values. The input information generation unit 102 may acquire information on the image findings from an external server (not illustrated) which provides a function of inferring image findings based on image feature values or may cause a module (an inference unit 106 or a second inference unit, for example) which is different from the input information generation unit 102 to perform inference.

The inference unit 106 performs inference based on the input information generated by the input information generation unit 102. The input information includes the image findings converted from the image feature values. Specifically, the inference unit 106 is an example of an inference unit which infers a diagnostic name derived from the medical image based on the image feature values.

The presentation probability acquisition unit 110 acquires presentation probabilities of candidates of reference information based on the image findings having likelihood attached thereto generated by the input information generation unit 102 and influence degrees acquired by the influence degree acquisition unit 108. The presentation probability acquisition unit 110 outputs the acquired presentation probabilities of the candidates of the reference information to a selection unit 112.

The medical diagnosis support apparatus 100 has a hardware configuration the same as that of the first embodiment illustrated in FIG. 2. Specifically, the functions (software) of the medical diagnosis support apparatus 100 and a process in a flowchart of FIG. 3 are realized when a CPU 1001 executes programs stored in a main memory 1002 and a magnetic disk 1003. The medical diagnosis support apparatus 100 may include a plurality of processors. For example, the medical diagnosis support apparatus 100 may individually include the input information generation unit 102 which infers image findings based on image feature values and an FPGA which programs a function of the inference unit 106 which infers a diagnostic name derived from a medical image.

FIG. 3 is a flowchart of a process performed by the medical diagnosis support apparatus 100 of the second embodiment. Detailed descriptions of processes which are the same as those of the first embodiment are omitted by invoking the foregoing descriptions, and portions different from the first embodiment will be described hereinafter.

Processes in step S3000 and step S3010 are the same as those of the first embodiment.

In step S3020, the input information generation unit 102 converts clinical information acquired in step S3000 and image feature values acquired in step S3010 into image findings so as to generate input information. Specifically, the input information generation unit 102 acquires information on findings by performing inference on the image feature values acquired in step S3010. In the second embodiment, the input information generation unit 102 performs the inference based on the image feature values and converts the image findings into image findings having likelihood attached thereto, for example.

It is assumed here that image findings to be acquired as a result of conversion from image feature values $\{i_1, i_2, \ldots, i_M\}$ correspond to a shape ($F_1$: $f_{11}$, $f_{12}$, $f_{13}$, and $f_{14}$). The input information generation unit 102 outputs likelihood of $f_{11}$, $f_{12}$, $f_{13}$, and $f_{14}$ using the image feature values as input. Assuming that likelihood of $f_{11}$ is $L(f_{11})$, the following expression is satisfied: $L(f_{11})+L(f_{12})+L(f_{13})+L(f_{14})=1.0$. Various methods may be employed as a method of inference performed on image findings as long as values having likelihoods attached thereto may be output. In the second embodiment, a multivalued neural network is used. Furthermore, the converted image findings having likelihood attached thereto are denoted by "$F_1(\ )$" hereinafter. Specifically, the input information generation unit 102 acquires information on findings corresponding to the image feature values and acquires likelihood for representing the image feature values as the findings, that is, statistical information.

Then the input information generation unit 102 generates aggregate of the converted image findings and the clinical information as input information. The image findings having the likelihood attached thereto are used as the input information. For example, when the clinical information is $\{c_{12}, c_{22}, \ldots, c_1\}$ and the converted image findings are $\{F_1(\ ), F_2(\ ), \ldots\}$, input information E is represented as follows: $E_f=[c_{12}, c_{22}, \ldots, c_j, F_1(\ ), F_2(\ ), \ldots]$.

In step S3030, the inference unit 106 executes inference associated with an abnormal shadow of a lung which is a diagnostic target based on the input information generated in step S3020. As with the first embodiment, the Bayesian network is used as an inference method. Specifically, the inference unit 106 performs inference using information on the findings acquired based on the image feature values as the input information.

Since the values of the image findings are represented by the likelihood in the second embodiment, inference is performed for all combinations of the image findings and results of the inference are integrated using the likelihood. Here, a case where the image findings are $F_a\{f_1, f_{a2}\}$ and $F_b\{f_{b1}, f_{b2}\}$ and the clinical information is $\{c_j\}$ will be described as an example. First, the inference unit 106 generates tentative input information ($E_z$) taking all combinations of elements included in the input information into consideration. In this case, the inference unit 106 generates four tentative input information, that is, $E_1=\{f_{a1}, f_{b1}, c_j\}$, $E_2=\{f_{a1}, f_{b2}, c_j\}$, $E_3=[f_{a2}, f_{b1}, c_j]$, and $E_4=\{f_{a2}, f_{b2}, c_j\}$. Then the inference unit 106 acquires $P(d_s|E_x)$ using the individual tentative input information. Furthermore, the inference unit 106 performs integration of the individual $P(d_s|E_z)$ and the likelihood of the image findings and acquires values by adding results of the integration to one another as final inference results. In the example above, the inference unit 106 acquires "$L(f_{a1})\times L(f_{b1})\times P(d_s|E_1)+ \ldots +L(f_{a2})\times L(f_{a2})\times P(d_s|E_t)$" as final inference results $P(d_s|E_t)$. In the example above, the inference results may be represented by Expression 6 below.

[Math.5]

$$P(d_s|E_f)=\Sigma_{z=1}^{Z}[\{\pi_{f_{nk}\in E_x}L(f_{nk})\}P(d_s|E_z)] \quad (6)$$

Specifically, the inference unit 106 generates pieces of tentative input information including at least some of information on the findings included in the input information and infers a diagnostic name based on results of inference performed based on the plurality of tentative input information and the likelihood, that is, statistical information. Note that the inference unit 106 may not take values of the image findings which have likelihood equal to or smaller than a threshold value into consideration.

A process in step S3040 is the same as that of the first embodiment.

In step S3050, the presentation probability acquisition unit 110 acquires presentation probabilities using the likelihood of the image findings acquired in step S3020 and influence degrees acquired in step S3040. The presentation probability acquisition unit 110 acquires absolute values of the influence degrees of elements included in the clinical information as presentation probabilities. Furthermore, the presentation probability acquisition unit 110 acquires products of the likelihood of the image findings converted by the input information generation unit 102 and the absolute values of the influence degrees as presentation probabilities. Specifically, the presentation probability acquisition unit 110 acquires presentation probabilities $L(f_{nk})\times I(f_{nk})$ of the image findings based on the influence degrees and the likelihood which is an example of the statistical information.

Processes in step S3060 and step S3070 are the same as those of the first embodiment. Specifically, the selection unit 112 selects information to be presented as a reason for the inference in accordance with the degrees of influence to the inference of information on the findings included in the input information and the presentation probabilities which are values based on the statistical information for representing regions indicated by the image feature values by information on the findings. Then the display controller 114 presents the information selected by the selection unit 112 as the reason for the inference.

According to the second embodiment, the medical diagnosis support apparatus 100 converts a medical image into image findings in accordance with a result of image processing and uses the converted image findings and clinical information as input information. Then the medical diagnosis support apparatus 100 acquires presentation probabilities of elements of the input information and presents the image findings and the clinical information serving as reference information in accordance with the presentation probabilities. By this, a doctor, that is, a user, may recognize the reference information in a form of the image findings or the clinical information which is easily understandable by persons, and therefore, the doctor may use the reference information as support for diagnosis.

First Modification of Second Embodiment

In step S3020, the input information generation unit 102 acquires image findings having likelihood attached thereto by inference based on image feature values. However, the present invention is not limited to this, and as with the first embodiment, a similar case may be searched for to acquire information on findings or correlation ratios may be used to acquire information on the findings.

When information on findings is to be acquired by searching for a similar case, similarity degrees Sim ($T_x$) are acquired using the Mahalanobis generalized distance and an expression for acquiring presentation probabilities of Expression 3 may be used as likelihood of the findings.

When information on findings is to be acquired using correlation ratios, likelihood may be acquired in accordance with Expression 7 below, for example.

[Math. 6]

$$L(f_{nk}) = \frac{1}{M}\sum_{m=1}^{M} \eta_{mnk} \quad (7)$$

Second Modification of Second Embodiment

In step S3030, the tentative input information of all the combinations of the image findings is generated and results of inference using the tentative input information are integrated so that a final inference result is acquired. However, the tentative input information of all the combinations of the image findings may not be generated. For example, only values of image findings having the highest likelihood may be used in the inference.

Third Embodiment

In a third embodiment, a case where input information to be input to an inference unit 106 includes information on findings acquired based on image feature values and information on findings input by a doctor as supplemental information will be described as an example.

A medical diagnosis support apparatus 100 of the third embodiment includes components the same as those of the first embodiment illustrated in FIG. 1. Furthermore, the medical diagnosis support apparatus 100 has a hardware configuration the same as that of the first embodiment illustrated in FIG. 2. Specifically, the functions (software) of the medical diagnosis support apparatus 100 according to the third embodiment and a process in a flowchart of FIG. 3 are realized when a CPU 1001 executes programs stored in a main memory 1002 and a magnetic disk 1003.

FIG. 3 is a flowchart of a process performed by the medical diagnosis support apparatus 100 according to the third embodiment. Detailed descriptions of processes which are the same as those of the first embodiment are omitted by invoking the foregoing descriptions, and portions different from the first embodiment will be described hereinafter.

Processes in step S3000 and step S3010 are the same as those of the first embodiment.

In step S3020, the input information generation unit 102 generates input information based on clinical information acquired in step S3000, image findings included in supplemental information, and image feature values acquired in step S3010. It is assumed here that the clinical information acquired in step S3000 is $\{c_{12}, c_{22}, \ldots, c_J\}$, the image findings included in the supplemental information are $\{f_{11}, f_{31}\}$, and the image feature values acquired in step S3010 are $\{i_1, i_2, \ldots, i_M\}$. In this case, input information $E_f$ is represented as follows: $E_f = \{c_{12}, c_{22}, \ldots, c_J, f_{11}, f_{31}, i_1, i_2, \ldots, i_M\}$.

Processes in step S3030 and step S3040 are the same as those of the first embodiment.

In step S3050, a presentation probability acquisition unit 110 calculates presentation probabilities of candidates of reference information using influence degrees calculated in step S3040. The presentation probability acquisition unit 110 acquires the image findings and absolute values of the influence degrees of elements included in the clinical information as presentation probabilities. Furthermore, the presentation probability acquisition unit 110 converts the image feature values into image findings having the presentation probabilities attached thereto.

As with the first embodiment, a similar case is searched for and image findings based on image feature values are acquired in the third embodiment. Here, the image findings acquired by the search for a similar case and the image findings input by the doctor may coincide with each other. When the image findings coincide with each other as described above, the presentation probability acquisition unit 110 determines that the image findings acquired by the similar case search are not the candidates of the reference information, for example. It is assumed here that an image finding included in the input information is $f_{11}$ and an image finding having a presentation probability attached thereto included in (c) of FIG. 6 is acquired. In this case, since $f_{11}$ which is a value included in an image finding $F_1$ is input by the doctor, $f_{14}$ which is a value included in the image finding $F_1$ among the image findings having the presentation probabilities attached thereto is not determined as a candidate of reference information, and the presentation probability is set to 0, for example. Accordingly, the candidates of the reference information include only f11 included in the image finding $F_1$. A presentation probability of $f_{11}$ which is supplemental information corresponds to an absolute value of an influence degree.

Processes in step S3060 and step S3070 are the same as those of the first embodiment.

According to the third embodiment, the medical diagnosis support apparatus 100 determines that the image feature values, the image findings, and the clinical information are input information when the imago findings are included in the supplemental information. Thereafter, the inference is performed based on the input information and the degrees of influence to inference results of the elements of the input information are acquired. Furthermore, the medical diagnosis support apparatus 100 acquires the presentation probabilities using the influence degrees of the elements. However, when the image findings converted from the image feature values and the image findings included in the input information coincide with each other, the image findings included in the input information are preferentially used. By this, the doctor, that is a user, executes the inference using the image findings input by the doctor, and in addition, the reference information may be presented in a form of image findings or clinical information which is easily understandable by persons. Furthermore, the user may check a reason for the inference taking user's thinking into consideration.

Modification

The present invention may be realized when programs which realize at least one function of the foregoing embodiment are supplied to a system or an apparatus through a network or a storage medium and at least one processor included in a computer of the system or the apparatus read and execute the programs. Furthermore, the present invention may be realized by a circuit (an application specific integrated circuit (ASIC), for example) which realizes at least one function.

Each of the medical diagnosis support apparatuses according to the foregoing embodiments may be realized as a single apparatus, or a plurality of apparatuses may be combined with one another in a communication available manner. Both of the cases are included in embodiments of the present invention. The foregoing process may be executed by a common server apparatus or a common server group. A medical diagnosis support apparatus and a plurality of apparatuses included in a medical diagnosis support system may communicate with one another in a predetermined communication rate, and it is not necessarily the case that the medical diagnosis support apparatus and the medical diagnosis support system are installed in the same facility or the same country.

The embodiments of the present invention also includes a case where programs of software which realize functions in the foregoing embodiments are supplied to a system or an apparatus and a computer included in the system or the apparatus reads and executes codes of the supplied programs.

Accordingly, the program codes installed in the computer for realizing the processes of the embodiments by the computer are also included in the embodiments of the present invention. Furthermore, an OS or the like which operates in the computer performs a portion or all of actual processes in accordance with an instruction included in the programs read by the computer, and the functions of the embodiment described above are realized by the process.

Embodiments acquired by appropriately combining the foregoing embodiments are also included in the embodiments of the present invention.

According to an embodiment of the present Invention, information serving as a reason for inference may be presented using information on findings including content easily recognizable by the doctor, and therefore, the doctor may easily determine whether a result of the inference is useful for diagnosis.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-080650, filed Apr. 13, 2016, which is hereby incorporated by reference herein in its entirety.

The invention claimed is:

1. A medical diagnosis support apparatus comprising:
   one or more memories, and
   one or more processors in communication with the one or more memories, wherein the one or more memories and the one or more processors operate to implement:
   an image feature value acquisition unit configured to acquire, from a medical image, image feature values, wherein the image feature values are numerical values indicating features of a region included in the medical image;
   an inference unit configured to infer a diagnostic name derived from the medical image using the image feature values indicating the features of the region included in the medical image as an input of the inference;
   an acquisition unit configured to acquire information on findings, representing the features of the region included in the medical image by a language as candidates of reference information, which are converted from the image feature values used by the inference unit as the input of the inference; and
   a presentation control unit configured to present the information on the findings acquired by the acquisition unit as a reason for the inference performed by the inference unit.

2. The medical diagnosis support apparatus according to claim 1, wherein the one or more memories and the one or more processors operate to further implement a selection unit configured to select information to be presented by the presentation control unit as the reason for the inference from among the candidates of reference information used by the inference unit as input of the inference.

3. The medical diagnosis support apparatus according to claim 2, wherein the selection unit is configured to select information to be presented by the presentation control unit as the reason for the inference for the information used by the inference unit as the input of the inference in accordance with influence degrees which are degrees of influence to the inference probability of the diagnostic name.

4. The medical diagnosis support apparatus according to claim 3,
   wherein the selection unit is configured to select information to be presented by the presentation control unit as the reason for the inference in accordance with the influence degrees and statistical information for representing the features of the region indicated by the image feature values by the findings, and
   wherein the presentation control unit presents the reason for the inference selected by the selection unit.

5. The medical diagnosis support apparatus according to claim 4, wherein the acquisition unit is configured to acquire information on the findings associated with the image feature values, the information being included in input information which is aggregate of information to be used as an input of the inference.

6. The medical diagnosis support apparatus according to claim 5,
   wherein the acquisition unit is configured to acquire information on the findings associated with the image feature values included in the input information in accordance with information on findings used in a similar case having image feature values similar to the image feature values included in the input information, and
   wherein the selection unit is configured to select information to be presented as the reason for the inference based on similarity degrees between the image feature values included in the input information and the image feature values of the similar case, the similarity degrees being obtained by using the influence degrees as a weight, and the statistical information indicating frequency of association between the findings and the similar case.

7. The medical diagnosis support apparatus according to claim 4, wherein the inference unit is configured to perform inference using the information on the findings acquired by the acquisition unit based on the image feature values as an input.

8. The medical diagnosis support apparatus according to claim 7,
wherein the acquisition unit is configured to acquire information on the findings by performing inference on the individual image feature values and acquire statistical information for representing the features of the region indicated by the image feature values by information on the finding, and
wherein the selection unit selects information to be presented as the reason for the inference in accordance with the influence degrees and the statistical information acquired by the acquisition unit.

9. The medical diagnosis support apparatus according to claim 8, wherein the inference unit is configured to generate pieces of tentative input information including combinations of information on the findings included in the input information of the inference and infer a diagnostic name based on results of the inference for the pieces of tentative input information and the statistical information acquired by the acquisition unit.

10. The medical diagnosis support apparatus according to claim 4, wherein the selection unit is configured to use predetermined correlation ratios between the image feature values and the findings as statistical information for representing the features of the region indicated by the image feature values by the findings.

11. The medical diagnosis support apparatus according to claim 4, wherein the selection unit is configured to select, when the information on the findings acquired by the acquisition unit based on the image feature values includes a plurality of findings which are differently representing the same feature, information on one of the findings which has a higher presentation probability based on the influence degrees and the statistical information.

12. The medical diagnosis support apparatus according to claim 4, wherein the selection unit is configured not to select, when information on findings input by a user is included as the input of the inference performed by the inference unit, information on findings acquired by the acquisition unit for features represented by the information on the findings input by the user.

13. The medial diagnosis support apparatus according to claim 1, wherein the inference unit is configured to infer a diagnostic name derived from the medical image in accordance with medical information acquired in diagnoses performed on a patient and the information on the findings input by the user, and the image feature values indicating the features of the region included in the medical image.

14. The medical diagnosis support apparatus according to claim 1, wherein the presentation control unit is configured to present the information on the findings which is the reason for the inference by displaying the information in a display unit.

15. The medical diagnosis support apparatus according to claim 1, further comprising a display control unit configured to cause a display unit to display the medical image, the inferred diagnostic name, and the information on the findings which is the reason for the inference.

16. An information processing method of diagnosis support, the method comprising:
acquiring, from a medical image, image feature values, wherein the image feature values are numerical values indicating features of a region included in the medical image;
inferring a diagnostic name derived from the medical image based on the image feature values indicating the features of the region included in the medical image;
acquiring information on findings, representing the features of the region included in the medical image by a language as candidates of reference information, by converting the image feature values; and
presenting the acquired information on the findings as a reason for the inference.

17. An information processing method of diagnosis support, the method comprising:
acquiring, from a medical image, image feature values, wherein the image feature values are numerical values indicating features of a region included in the medical image;
inferring a diagnostic name derived from the medical image using the image feature values indicating the features of the region included in the medical image as an input;
acquiring information on findings, representing the features of the region included in the medical image by a language as candidates of reference information, by converting the image feature values that were input for the inference; and
presenting the acquired information on the findings as a reason for the inference.

18. An information processing method of diagnosis support, the method comprising:
acquiring, from a medical image, image feature values, wherein the image feature values are numerical values indicating features of a region included in the medical image;
acquiring information on findings, representing features of the region included in the medical image by a language as candidates of reference information, by converting the image feature values indicating the features of the region;
inferring a diagnostic name derived from the medical image using the information on the findings as an input; and
presenting the information on the findings as a reason for the inference.

19. A medical diagnosis support system comprising:
one or more memories, and
one or more processors in communication with the one or more memories, wherein the one or more memories and the one or more processors operate to implement:
an image feature value acquisition unit configured to acquire, from a medical image, image feature values, wherein the image feature values are numerical values indicating features of a region included in the medical image;
an inference unit configured to infer a diagnostic name derived from the medical image based on the image feature values indicating the features of the region included in the medical image;
a presentation control unit configured to present information on findings, representing the features of the region included in the medical image by a language as reference information, as a reason for the inference performed by the inference unit, wherein the information on the findings is generated by converting the image feature values; and an acquisition unit configured to acquire the information on the findings based on the image feature values.

20. A medical diagnosis support apparatus comprising:

one or more memories, and one or more processors in communication with the one or more memories, wherein the one or more memories and the one or more processors operate to implement:

an image feature value acquisition unit configured to acquire, from a medical image, image feature values, wherein the image feature values are numerical values indicating features of a region included in the medical image;

an inference unit configured to infer a diagnostic name derived from the medical image using the image feature values indicating the features of the region included in the medical image as an input of an inference;

an acquisition unit configured to acquire information on findings, representing the features of the region included in the medical image by a language as candidates of reference information, which are converted from the image feature values used by the inference unit as the input of the inference; and a presentation control unit configured to present the information on the findings acquired by the acquisition unit.

21. A medical diagnosis support apparatus comprising:

one or more memories, and one or more processors in communication with the one or more memories, wherein the one or more memories and the one or more processors operate to implement:

an image feature value acquisition unit configured to acquire, from a medical image, image feature values, wherein the image feature values are numerical values indicating features of a region included in the medical image;

an acquisition unit configured to acquire information on findings, representing features of the region included in the medical image by a language as candidates of reference information, by performing inference on the image feature values indicating the features of the region included in the medical image;

an inference unit configured to infer a diagnostic name derived from a medical image using the information on the findings acquired by the acquisition unit based on the image feature values as an input; and a presentation control unit configured to present the information on the findings acquired by the acquisition unit.

22. A medical diagnosis support apparatus comprising:

one or more memories, and one or more processors in communication with the one or more memories, wherein the one or more memories and the one or more processors operate to implement:

an inference unit configured to infer a diagnostic name derived from a medical image as an input of an inference;

an acquisition unit configured to acquire information on findings, representing features of a region included in the medical image by a language as candidates of reference information, based on the medical image used by the inference unit as the input of the inference; and a presentation control unit configured to present the information on the findings acquired by the acquisition unit.

23. The medical diagnosis support apparatus according to claim 22, wherein the acquisition unit is configured to acquire the information on the findings by inferring the findings based on the medical image as the input of the inference.

24. The medical diagnosis support apparatus according to claim 22, wherein the acquisition unit is configured to acquire the information on the findings by inferring the findings based on a feature amount representing features of a region included in the medical image as the input of the inference.

25. The medical diagnosis support apparatus according to claim 22, wherein the inference unit is configured to perform inference based on at least one of a Bayesian network, a support vector machine, and a neural network.

26. The medical diagnosis support apparatus according to claim 22, further comprising a selection unit configured to select information to be presented by the presentation control unit as a reason for the inference based on the influence that is a degree of an influence on the inference of the diagnostic name with respect to the medical image used by the inference unit as the input of the inference.

* * * * *